(12) United States Patent
Matsuo et al.

(10) Patent No.: US 8,905,919 B2
(45) Date of Patent: Dec. 9, 2014

(54) ENDOSCOPE

(71) Applicant: Olympus Medical Systems Corp., Tokyo (JP)

(72) Inventors: Shigeki Matsuo, Fukuoka (JP); Suguru Okaniwa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/054,352

(22) Filed: Oct. 15, 2013

(65) Prior Publication Data

US 2014/0088356 A1 Mar. 27, 2014

Related U.S. Application Data

(63) Continuation of application No. PCT/JP2013/063824, filed on May 17, 2013.

(30) Foreign Application Priority Data

Aug. 14, 2012 (JP) ................................. 2012-179845

(51) Int. Cl.
| | | |
|---|---|---|
| *A61B 1/00* | (2006.01) | |
| *A61B 1/005* | (2006.01) | |
| *A61B 1/008* | (2006.01) | |
| *A61B 1/05* | (2006.01) | |

(52) U.S. Cl.
CPC ............. *A61B 1/0057* (2013.01); *A61B 1/0056* (2013.01); *A61B 1/0055* (2013.01); *A61B 1/008* (2013.01); *A61B 1/05* (2013.01)
USPC ............................ 600/141; 600/139; 600/146

(58) Field of Classification Search
CPC ... A61B 1/0055; A61B 1/0052; A61B 1/0051

USPC .......................................... 600/139, 141, 146
See application file for complete search history.

(56) References Cited

U.S. PATENT DOCUMENTS

| | | | | |
|---|---|---|---|---|
| 3,799,151 A | * | 3/1974 | Fukaumi et al. | ............... 600/142 |
| 5,179,935 A | * | 1/1993 | Miyagi | ........................ 600/142 |

(Continued)

FOREIGN PATENT DOCUMENTS

| | | |
|---|---|---|
| JP | A-10-234653 | 9/1998 |
| JP | A-2004-298446 | 10/2004 |

(Continued)

OTHER PUBLICATIONS

International Search Report issued in Application No. PCT/JP2013/063824; Dated Jun. 11, 2013 (With Translation).

*Primary Examiner* — Anhtuan T Nguyen
*Assistant Examiner* — Rynae Boler
(74) *Attorney, Agent, or Firm* — Oliff PLC

(57) ABSTRACT

An endoscope includes a distal rigid portion, a bending portion comprising a first bending portion and a second bending portion and a flexible tube portion. The endoscope further includes an operation wire, a wire guide member, a bending operation portion. The endoscope further includes a regulation wire, the regulation wire being longer than the bending portion, the regulation wire being inserted through the first bending portion and the second bending portion, the regulation wire being provided to face the operation wire in the diametrical direction of the bending portion, the regulation wire regulating the bending of the bending portion so that the second bending portion is bent in a direction opposite to the bending direction of the first bending portion and the bending portion is bent in an S-shape when the first bending portion is bent.

7 Claims, 12 Drawing Sheets

(56) References Cited

U.S. PATENT DOCUMENTS

| | | | | |
|---|---|---|---|---|
| 5,448,989 | A * | 9/1995 | Heckele | 600/142 |
| 7,491,166 | B2 * | 2/2009 | Ueno et al. | 600/107 |
| 2009/0287054 | A1 | 11/2009 | Dejima et al. | |
| 2011/0295069 | A1 | 12/2011 | Ouchi | |

FOREIGN PATENT DOCUMENTS

| | | |
|---|---|---|
| JP | A-2005-261513 | 9/2005 |
| JP | A-2009-279405 | 12/2009 |
| WO | WO 2011/114570 A1 | 9/2011 |

* cited by examiner

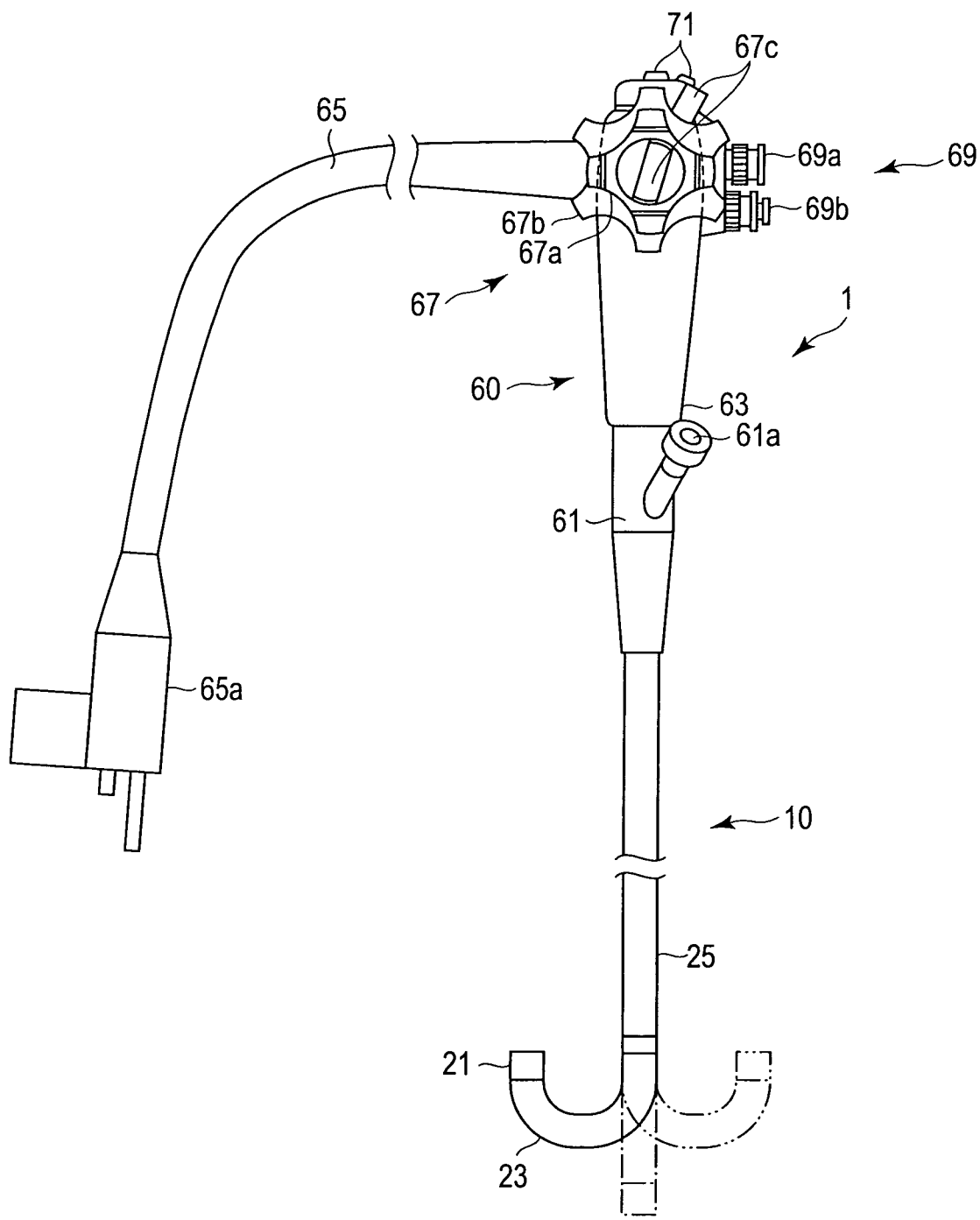
F I G. 1

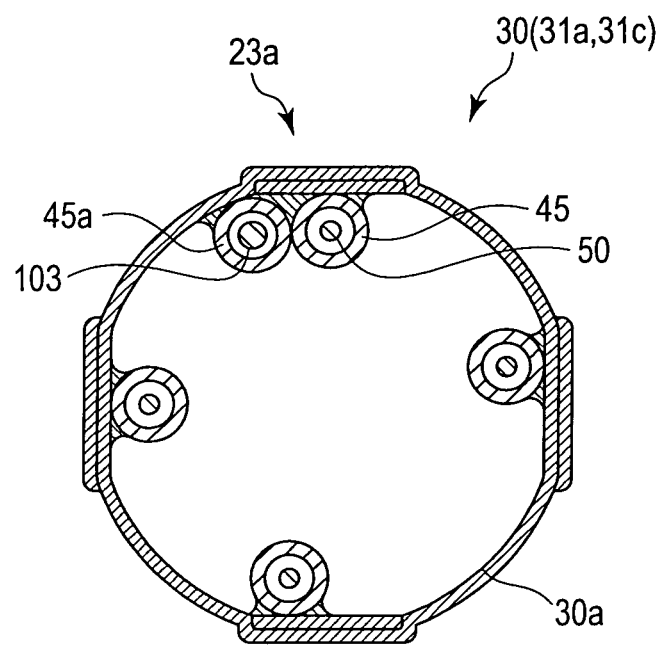
F I G. 3C
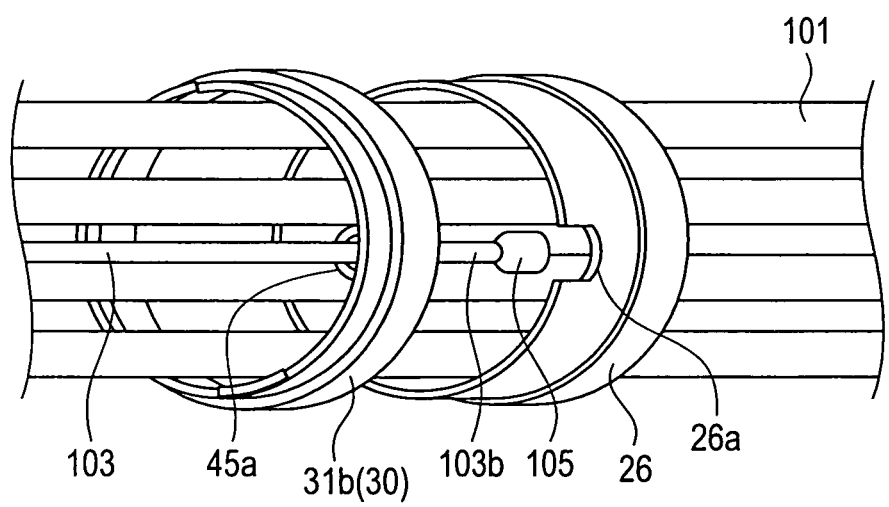
F I G. 4

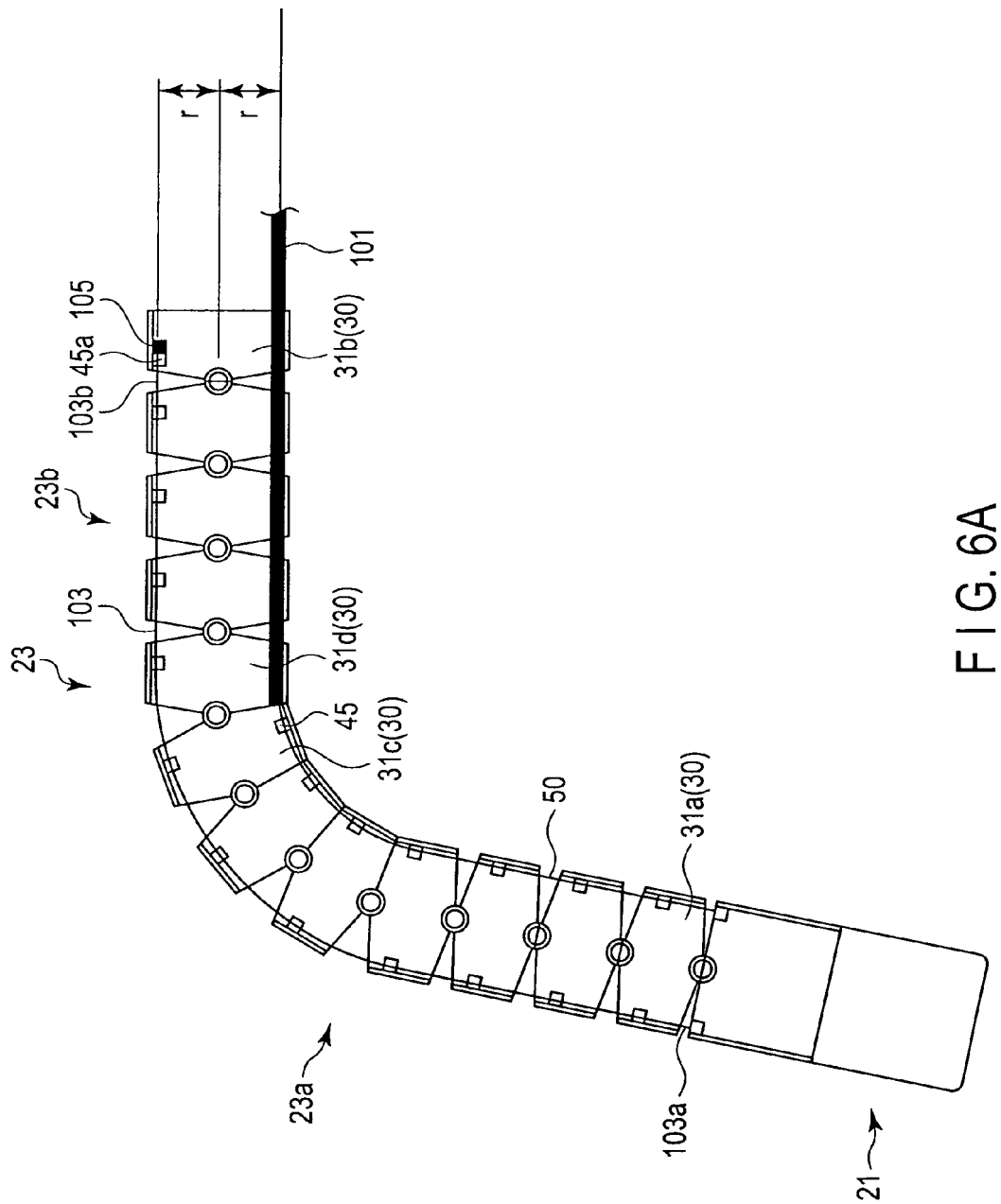
F I G. 6A

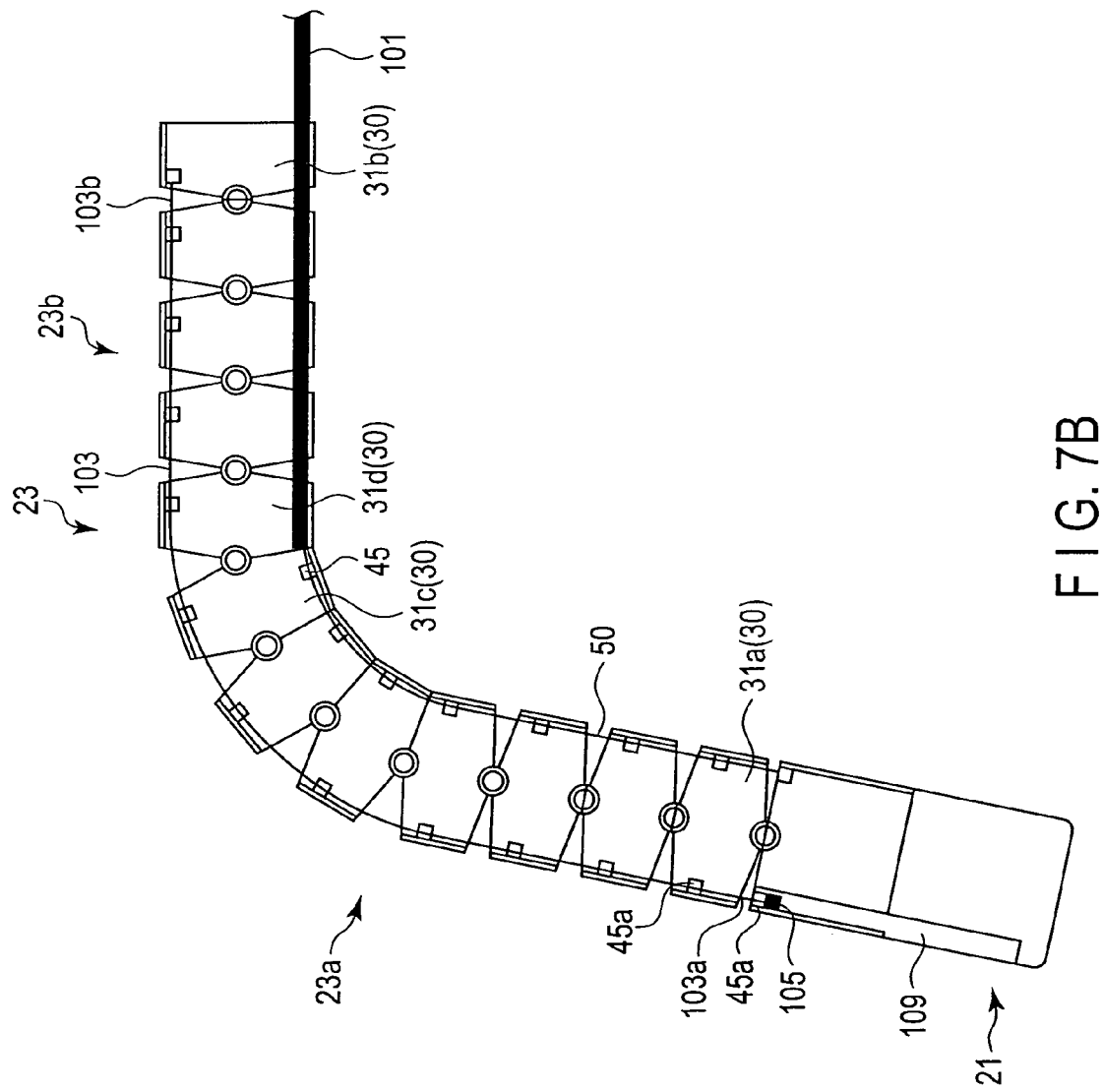
F I G. 7B

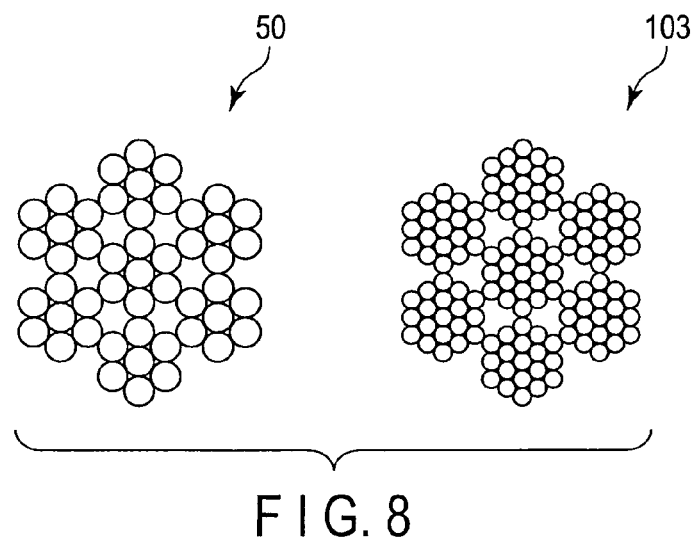
F I G. 8
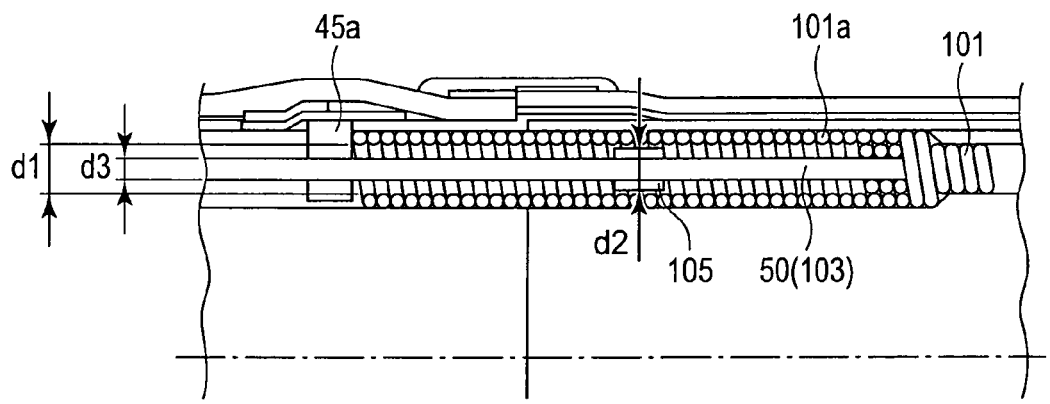
F I G. 9

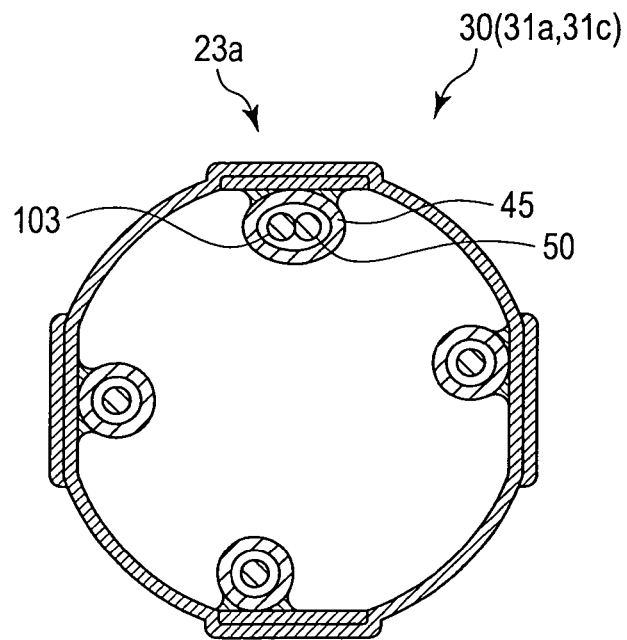
F I G. 10A
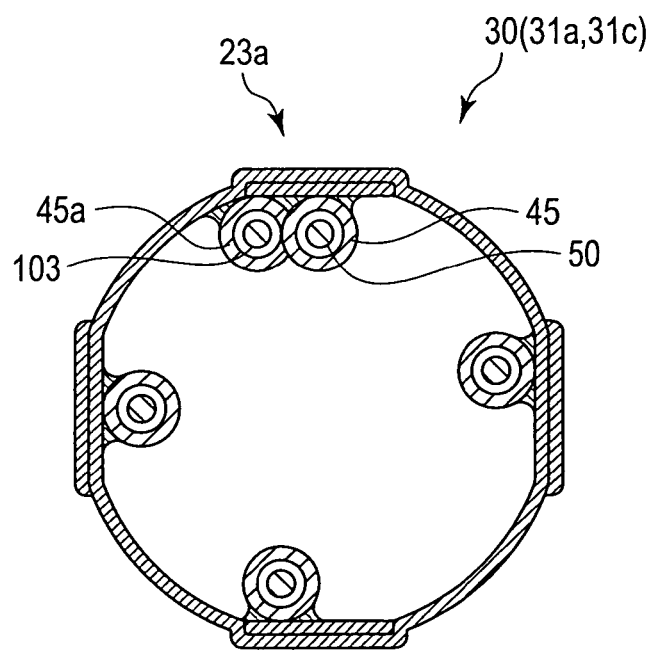
F I G. 10B

ENDOSCOPE

CROSS-REFERENCE TO RELATED APPLICATIONS

This application is a Continuation Application of PCT Application No. PCT/JP2013/063824, filed May 17, 2013 and based upon and claiming the benefit of priority from prior Japanese Patent Application No. 2012-179845, filed Aug. 14, 2012, the entire contents of all of which are incorporated herein by reference.

BACKGROUND OF THE INVENTION

1. Field of the Invention

The present invention relates to an endoscope having a bending portion which can be bent in an S-shape.

2. Description of the Related Art

For example, Jpn. Pat. Appln. KOKAI Publication No. 2005-261513 discloses an endoscope. This endoscope has a first bending portion provided at the distal end of an insertion portion, a second bending portion which is provided at the proximal end of the insertion portion and which is coupled to the first bending portion, and an operation portion which operates the first bending portion. The second bending portion is bent by external force.

For example, Jpn. Pat. Appln. KOKAI Publication No. 10-234653 discloses another endoscope. A bending portion of the endoscope is bent preferentially from the distal end portion side of the bending portion.

For example, Jpn. Pat. Appln. KOKAI Publication No. 2004-298446 discloses yet another endoscope. This endoscope has a first bending portion, a second bending portion coupled to the proximal end portion of the first bending portion, a first operation portion which operates the first bending portion, and a second operation portion which operates the second bending portion. Thus, the endoscope has the operation portions which respectively operate the bending portions.

BRIEF SUMMARY OF THE INVENTION

An aspect of an endoscope of the present invention includes distal rigid portion comprising an imaging unit configured to image an observation target; a bending portion comprising a first bending portion coupled to the distal rigid portion and a second bending portion coupled to the proximal end portion of the first bending portion; a flexible tube portion coupled to the proximal end portion of the second bending portion; an operation wire which is connected to the distal rigid portion and which is inserted through the first bending portion, the second bending portion, and the flexible tube portion; a wire guide member comprising a distal end fixed to the inside of the distal end of the second bending portion, the wire guide member being inserted through the second bending portion and the flexible tube portion, the wire guide member guiding the operation wire when the operation wire is inserted through the wire guide member; a bending operation portion which is connected to the operation wire and which bends and operates the first bending portion when the bending operation portion pulls the operation wire; and a regulation wire, the regulation wire being longer than the bending portion, the regulation wire being inserted through the first bending portion and the second bending portion, the regulation wire being provided to face the operation wire in the diametrical direction of the bending portion, the regulation wire regulating the bending of the bending portion so that the second bending portion is bent in a direction opposite to the bending direction of the first bending portion and the bending portion is bent in an S-shape when the first bending portion is bent.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing an endoscope according to a first embodiment of the present invention;

FIG. 3C is a front view of a joint ring through which an operation wire and a regulation wire are inserted;

FIG. 4 is a perspective view simply showing a coupling structure between a joint ring provided at the proximal end portion of the bending portion and a mouthpiece of a flexible tube portion;

FIG. 6A is a schematic diagram in which the first bending portion alone is bent;

FIG. 7B is a schematic diagram in which the first bending portion alone is bent;

FIG. 8 is a diagram showing the structures of the operation wire and the regulation wire according to a second modification;

FIG. 9 is a diagram showing how the operation wire doubles as the regulation wire according to a third modification;

FIG. 10A is a diagram showing a modification of a holding member according to a fourth modification; and FIG. 10B is a diagram showing a modification of the holding member according to a fifth modification.

DETAILED DESCRIPTION OF THE INVENTION

Hereinafter, embodiments of the present invention will be described in detail with reference to the drawings.

[First Embodiment]

[Configuration]

A first embodiment is described with reference to FIG. 1, FIG. 2, FIG. 3A, FIG. 3B, FIG. 3C, FIG. 4, FIG. 5A, FIG. 5B, FIG. 6A, and FIG. 6B.

Figure 5A:
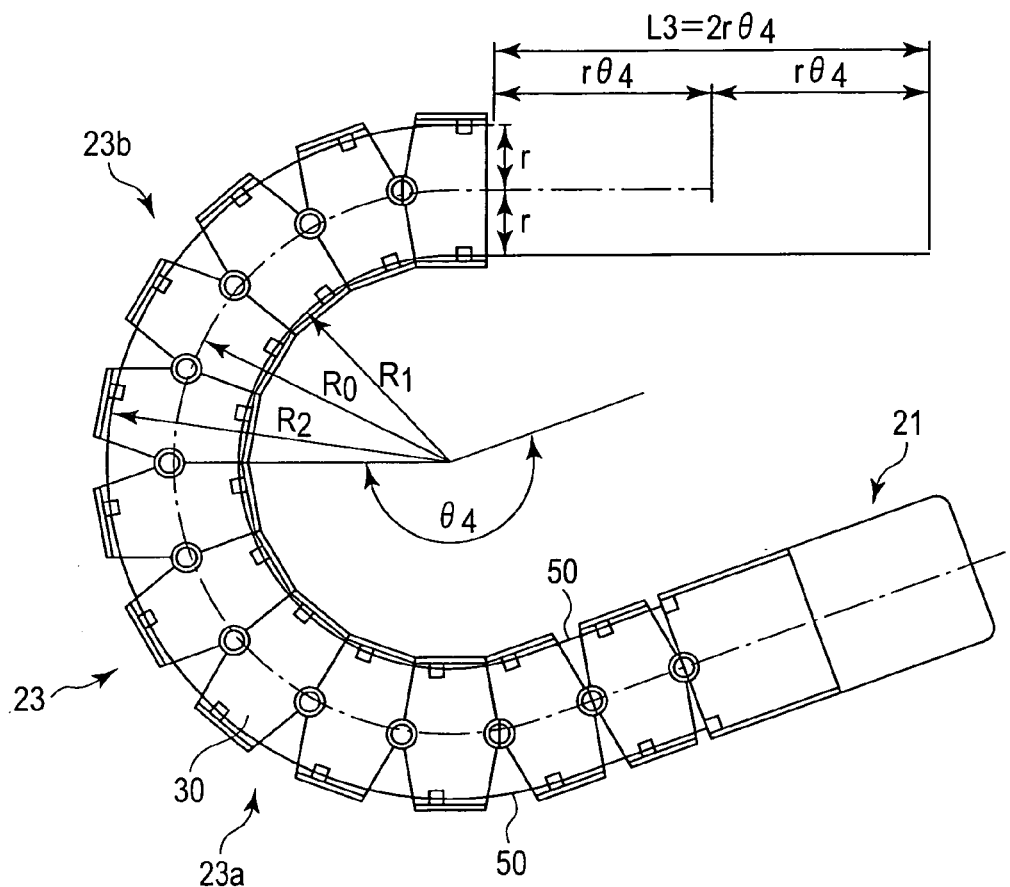
FIG. 5A is a schematic diagram for calculating a difference L3 between a contracted inner operation wire and a stretched outer operation wire when the bending portion is bent.

As a wire guide member 101 is not shown in, for example, FIG. 5A, some components are not shown for simplicity in some of the drawings.

In the present embodiment, the longitudinal direction of an insertion portion 10, the longitudinal direction of a bending portion 23, and the axial direction of the wire guide member 101 are the same direction.

[Endoscope 1]

As shown in FIG. 1, an endoscope 1 has the elongate insertion portion 10 to be inserted into, for example, a body cavity of a patient, and an operation portion 60 which is coupled to the proximal end portion of the insertion portion 10 and which operates the endoscope 1.

[Insertion portion 10]

The insertion portion 10 has a distal rigid portion 21, a bending portion 23, and a flexible tube portion 25 from the distal end portion side of the insertion portion 10 to the proximal end portion side of the insertion portion 10. The proximal end portion of the distal rigid portion 21 is coupled to the distal end portion of the bending portion 23, and the proximal end portion of the bending portion 23 is coupled to the distal end portion of the flexible tube portion 25.

The distal rigid portion 21 functions as the distal end of the endoscope 1 and the distal end of the insertion portion 10, and is rigid. The distal rigid portion 21 has an unshown imaging unit to image an observation target.

The bending portion 23 will be described later.

The flexible tube portion 25 has desired flexibility. Therefore, the flexible tube portion 25 is bent by external force. The flexible tube portion 25 is a tubular member extending from a later-described main body portion 61 in the operation portion 60.

[Operation portion 60]

The operation portion 60 has the main body portion 61 from which the flexible tube portion 25 extends, a grasping portion 63 which is coupled to the proximal end portion of the main body portion 61 and which is grasped by an operator to operate the endoscope 1, and a universal cord 65 connected to the grasping portion 63.

[Main body portion 61]

The main body portion 61 has a treatment tool insertion opening 61a. The treatment tool insertion opening 61a is coupled to the proximal end portion of an unshown treatment tool insertion channel. The treatment tool insertion channel is provided from the flexible tube portion 25 to the distal rigid portion 21 inside the insertion portion 10. The treatment tool insertion opening 61a is an insertion opening to insert an unshown endoscope treatment tool into the treatment tool insertion channel. The unshown endoscope treatment tool is inserted into the treatment tool insertion channel from the treatment tool insertion opening 61a, and pressed to the side of the distal rigid portion 21. The unshown endoscope treatment tool is then projected from an unshown distal opening portion of the treatment tool insertion channel provided in the distal rigid portion 21.

[Grasping portion 63]

The grasping portion 63 has a bending operation portion 67 which bends and operates the bending portion 23. The bending operation portion 67 has a horizontal bending operation knob 67a which is operated to horizontally bend the bending portion 23, and a vertical bending operation knob 67b which is operated to vertically bend the bending portion 23. The bending operation portion 67 further has a fixing knob 67c which fixes the position of the bent bending portion 23.

The horizontal bending operation knob 67a is connected to an unshown horizontal bending operation mechanism driven by the horizontal bending operation knob 67a. The vertical bending operation knob 67b is connected to an unshown vertical bending operation mechanism driven by the vertical bending operation knob 67b. The vertical bending operation mechanism and the horizontal bending operation mechanism are provided in the operation portion 60.

Figure 2:
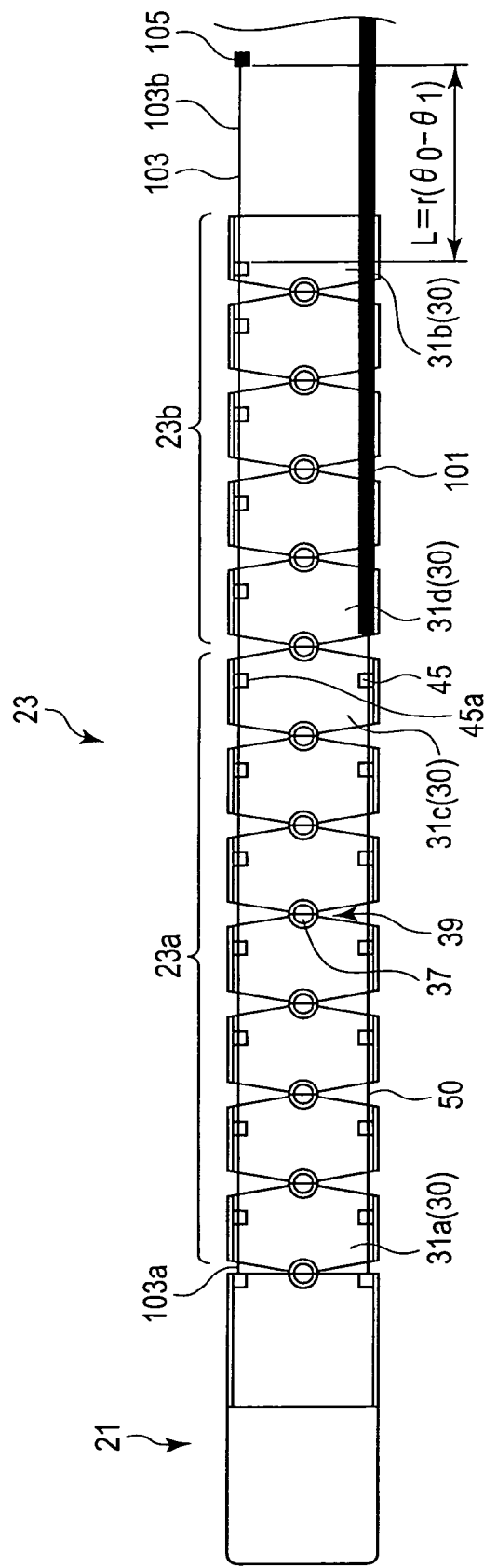
FIG. 2 is a diagram simply showing the structure of a bending portion.

The horizontal bending operation mechanism is connected to the proximal end portion of a later-described operation wire 50 inserted through the flexible tube portion 25 and the bending portion 23. As shown in FIG. 2, the distal end portion of this operation wire 50 is connected to the distal rigid portion 21, for example, by solder.

The vertical bending operation mechanism is connected to the proximal end portion of an operation wire 50 inserted through the flexible tube portion 25 and the bending portion 23. The operation wire 50 connected to the vertical bending operation mechanism is different from the operation wire 50 connected to the horizontal bending operation mechanism. The distal end portion of the operation wire 50 connected to the vertical bending operation mechanism is connected to the distal rigid portion 21, for example, by solder.

The horizontal bending operation knob 67a horizontally bends the bending portion 23 via the horizontal bending operation mechanism and the operation wire 50. The vertical bending operation knob 67b vertically bends the bending portion 23 via the vertical bending operation mechanism and the operation wire 50.

The grasping portion 63 also has a switch section 69. The switch section 69 is operated by the hand of the operator when the grasping portion 63 is grasped by the operator. The switch section 69 has a suction switch 69a and an air/water supply switch 69b. The suction switch 69a is operated when the endoscope 1 sucks, for example, mucus or fluid from an unshown suction opening provided in the distal rigid portion 21 via an unshown suction channel. The air/water supply switch 69b is operated when fluid is supplied from an unshown air/water supply channel to ensure an imaging field of the unshown imaging unit provided in the distal rigid portion 21. The fluid includes water and gasses.

The grasping portion 63 also has various buttons 71 for endoscopic photography.

[Universal Cord 65]

The universal cord 65 has a connection portion 65a connected to an unshown video processor or light source device.

[Bending Portion 23]

Now, the bending portion 23 is described with reference to FIG. 2.

The bending portion 23 is bent in a desired direction, for example, in vertical and horizontal directions by the operation of the bending operation portion 67. When the bending portion 23 is bent, the position and direction of the distal rigid portion 21 are changed, the observation target is caught in the imaging field of the imaging unit, and the observation target is illuminated by illumination light.

As shown in FIG. 2, the bending portion 23 is composed of joint rings 30 arrayed along the longitudinal direction of the insertion portion 10. The joint ring 30 has a substantially cylindrical (annular) shape. The adjacent joint rings 30 (front and rear joint rings along the longitudinal direction of the insertion portion 10) are rotatably coupled to each other by a later-described coupling portion 39. As the joint rings 30 are rotatably coupled to each other, the bending portion 23 which can be bent (rotatable) as described above is formed.

[Joint Rings 30]

The joint rings 30 are described with reference to FIG. 3A and FIG. 3B.

As described above, the joint ring 30 has a substantially cylindrical shape. The joint ring 30 is made of a rigid material such as a metal. The joint ring 30 is molded by, for example, a pressed sheet metal or forging. Such joint rings 30 are arrayed along the longitudinal direction of the insertion portion 10, as shown in FIG. 2. The adjacent joint rings 30 (front and rear joint rings along the insertion direction of the insertion portion 10) are rotatably coupled to each other by the coupling portion 39 as described above.

The joint ring 30 has two projecting pieces (front hinge mounts) 33 provided on the distal end portion side (left side in FIG. 3A and FIG. 3B) of the joint ring 30. The projecting pieces 33 are parts of the joint ring 30 that project forward (to the distal end portion side of the bending portion 23). The projecting pieces 33 are formed into planar shape. Each of the projecting pieces 33 has a through-hole 33a which passes through the projecting piece 33 in the thickness direction of the projecting piece 33. Two projecting pieces 33 are located substantially 180° apart from each other in the circumferential direction of the joint ring 30.

The joint ring 30 also has two projecting pieces (rear hinge mounts) 35 provided on the rear end portion side (right side in FIG. 3A and FIG. 3B) of the joint ring 30. The projecting pieces 35 show parts of the joint ring 30 that project rearward (to the proximal side of the bending portion 23). The projecting pieces 33 are formed into a planar shape. Each of the projecting pieces 35 has a step which has substantially the same thickness as the thickness of the projecting piece 33. Each of the projecting pieces 35 also has a through-hole 35a which passes through the projecting piece 33 in the thickness direction of the projecting piece 33. Two projecting pieces 35 are located substantially 180° apart from each other in the circumferential direction of the joint ring 30.

The projecting piece 33 and the projecting piece 35 are located substantially 90° apart from each other in the circumferential direction of the joint ring 30.

In the projecting piece 35 provided in the joint ring 30 on the side of the flexible tube portion 25 (the proximal end portion of the insertion portion 20) and in the projecting piece 33 provided in the joint ring 30 on the side of the distal rigid portion 21 (the distal end portion of the insertion portion 20), rivets 37 shown in FIG. 2 are inserted into the through-holes 33a and 35a. The rivet 37 functions as a rotation member (pivot shaft) which rotatably couples the joint rings 30. Thus, the joint ring 30 on the side of the flexible tube portion 25 and the joint ring 30 on the side of the distal rigid portion 21 are coupled to each other by the rivet 37, and pivotally supported rotatably around the rivet 37. In this way, the rivet 37 is formed as a rotational support shaft provided between the projecting piece 33 and the projecting piece 35.

In other words, the projecting piece 33, the projecting piece 35, and the rivet 37 function as the coupling portion 39 which couples the joint ring 30 on the side of the flexible tube portion 25 and the joint ring 30 on the side of the distal rigid portion 21.

When the joint rings 30 are coupled by the rivet 37, the projecting piece 33 provided in the joint ring 30 on the side of the flexible tube portion 25 is stacked on the projecting piece 35 provided in the joint ring 30 on the side of the distal rigid portion 21.

In the bending portion 23 according to the present embodiment, the rivets 37 are alternately located substantially 90° away from each other on the front and rear sides of each joint ring 30. Thus, the bending portion 23 can be bent in four vertical and horizontal directions.

Figure 3A:
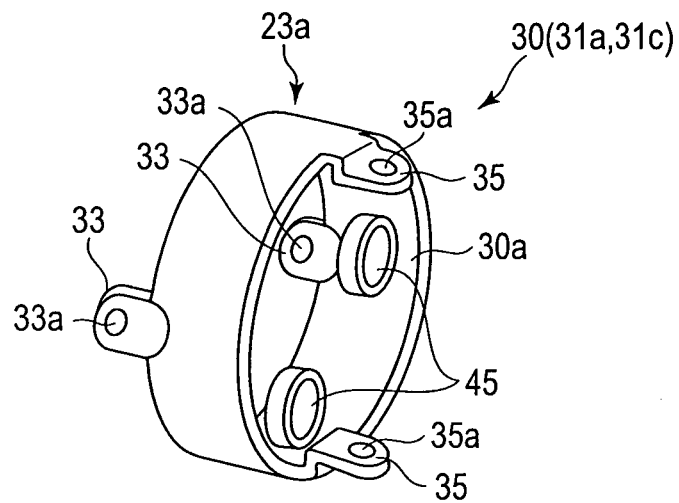
FIG. 3A is a perspective view of a joint ring provided in a first bending portion.
Figure 3B:
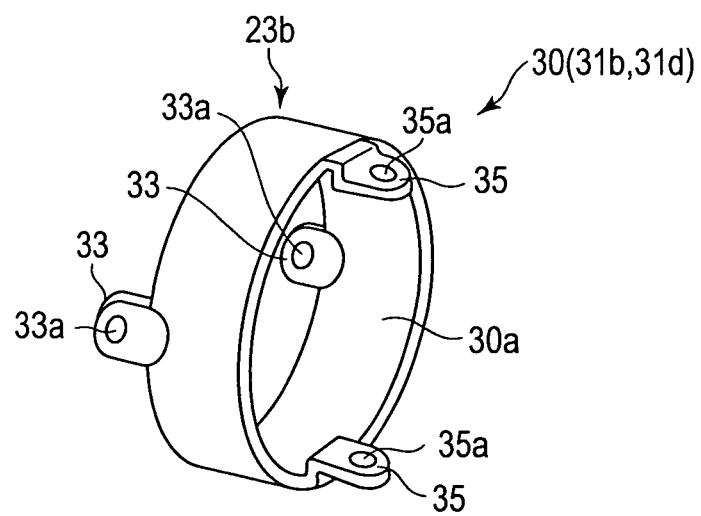
FIG. 3B is a perspective view of a joint ring provided in a second bending portion.

In the present embodiment, the joint ring 30 provided at the distal end portion of the bending portion 23 as shown in FIG. 2 and FIG. 3A is a distal end portion joint ring (hereinafter referred to as a joint ring 31a), and the joint ring 30 provided at the proximal end portion of the bending portion 23 as shown in FIG. 2 and FIG. 3B is a proximal end portion joint ring (hereinafter referred to as a joint ring 31b). As shown in FIG. 2, the joint ring 31a is coupled to the distal rigid portion 21. As shown in FIG. 4, the joint ring 31b is fitted into a mouthpiece 26 of the flexible tube portion 25, and is then coupled to the mouthpiece 26 of the flexible tube portion 25, for example, by screws or adhesion.

The joint ring 30 provided between the joint ring 31a and the joint ring 31b as shown in FIG. 2 and FIG. 3A is a distal end portion side joint ring (hereinafter referred to as a joint ring 31c). This joint ring 31c has a later-described holding member 45. The joint ring 30 provided between the joint ring 31c and the joint ring 31b as shown in FIG. 2 and FIG. 3B is a proximal end portion side joint ring (hereinafter referred to as a joint ring 31d). The later-described wire guide member 101 is inserted through the joint ring 31d. The joint ring 31c provided closest to the flexible tube portion 25 and the joint ring 31d provided closest to the distal rigid portion 21 are rotatably coupled to each other as described above.

[First Bending Portion 23a, Second Bending Portion 23b]

Figure 6B:
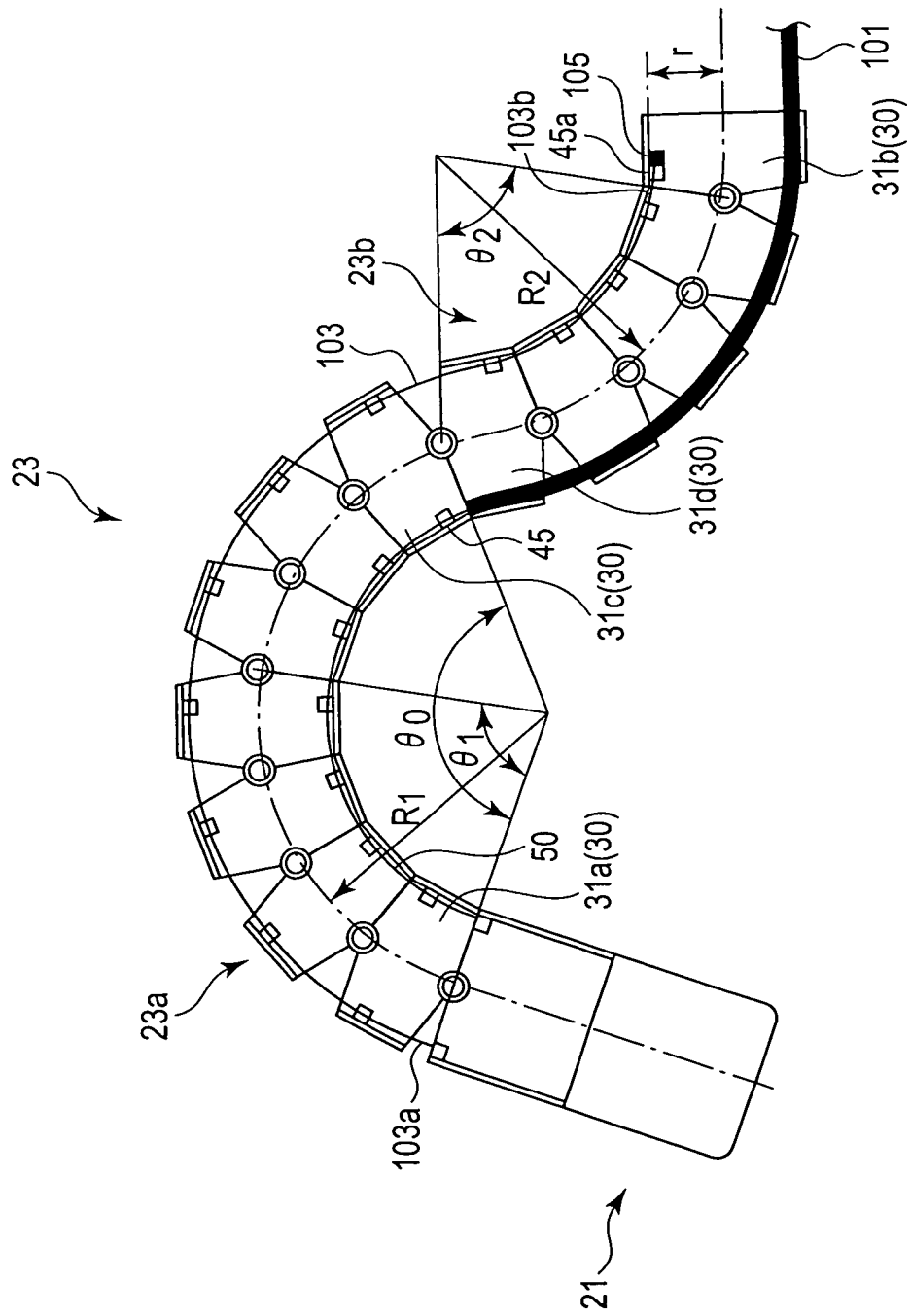
FIG. 6B is a schematic diagram in which the bending portion is bent in an S-shape.

As shown in FIG. 2, the bending portion 23 has a first bending portion 23a coupled to the distal rigid portion 21, and a second bending portion 23b coupled to the proximal end portion of the first bending portion 23a. The first bending portion 23a is formed by the joint rings 30 having the joint rings 31a and the joint rings 31c. The first bending portion 23a is operated and bent by the bending operation portion 67 when the bending operation portion 67 pulls the operation wire 50. The proximal end portion of the second bending portion 23b is coupled to the flexible tube portion 25. The second bending portion 23b is formed by the joint rings 30 having the joint rings 31d and the joint rings 31b. The second bending portion 23b is bent by a later-described regulation wire 103 in a direction opposite to the bending direction of the first bending portion 23a as shown in FIG. 6B. In the second bending portion 23b, the joint ring 31d coupled to the joint ring 31c functions as the distal end portion of the second bending portion 23b. The joint ring 31b functions as the proximal end portion of the second bending portion 23b, and is coupled to the mouthpiece 26 of the flexible tube portion 25 as shown in FIG. 4.

[Wire Guide Member 101]

As shown in FIG. 2, the second bending portion 23b has the wire guide member 101 so that the wire guide member 101 is inserted through the second bending portion 23b. The distal end portion of the wire guide member 101 is fixed to the inside of the distal end portion of the second bending portion 23b, that is, an inner circumferential surface 30a of the joint ring 31d coupled to the joint ring 31c. Although described later, the proximal end portion of the wire guide member 101 is inserted through the flexible tube portion 25. The wire guide member 101 is provided in the second bending portion 23b alone, that is, in the joint ring 31b and the joint ring 31d, and is not provided in the first bending portion 23a. In other words, the bending portion 23 in which the wire guide member 101 is provided functions as the second bending portion 23b. In the bending portion 23, the second bending portion 23b has the wire guide member 101 provided therein and is therefore more rigid than the first bending portion 23a. Thus, the bending portion 23 is bent from the distal end portion of the bending portion 23. In other words, the first bending portion 23a is bent before the second bending portion 23b.

The wire guide member 101 guides the operation wire 50 when the operation wire 50 is inserted through the wire guide member 101. The wire guide member 101 functions as an elastic tubular member. The wire guide member 101 is inserted through the second bending portion 23b, the flexible tube portion 25, and the main body portion 61.

The operation wire 50 is inserted through the wire guide member 101 so that the operation wire 50 is movable back and forth in the axial direction of the operation wire 50. The wire guide member 101 functions as a wire insertion member through which the operation wire 50 is inserted. The wire guide member 101 protects the operation wire 50 against inner objects other than the operation wire 50. The inner objects mean members such as a suction tube provided inside the insertion portion 20. Since the wire guide member 101 is provided in the second bending portion 23b as described above, the wire guide member 101 guides and protects the operation wire 50 in the second bending portion 23b. The wire guide member 101 has, for example, a coil sheath wound around the operation wire 50. One operation wire 50 is inserted through one wire guide member 101.

[Holding Member 45]

In this case, as shown in FIG. 2 and FIG. 3A, the distal end portion side of the operation wire 50 projects from the wire guide member 101, and is held by the holding members 45 in the first bending portion 23a. As shown in FIG. 2 and FIG. 3A, the holding members 45 are provided in the first bending portion 23a, that is, the inner circumferential surfaces 30a of the joint rings 31a and 31c, and are not provided in the second bending portion 23b, that is, the joint rings 31b and 31d. The holding member 45 functions as a receiving member to receive the operation wire 50. The holding member 45 is made of a rigid material such as a metal. As shown in FIG. 3A and FIG. 3C, the holding member 45 has, for example, a cylindrical shape. The holding members 45 are fixed to the inner circumferential surface 30a, for example, by welding. The holding members 45 are aligned with the projecting pieces 33 and 35 in the longitudinal direction of the bending portion 23. Therefore, in the joint rings 31a and 31c, four holding members 45 are provided 90° apart in the circumferential direction as shown in FIG. 3C. The holding members 45 provided in the joint rings 31a and 31c are aligned in the longitudinal direction of the bending portion 23.

[Operation Wire 50]

The operation wire 50 is inserted through the holding members 45 so that the operation wire 50 is movable back and forth in the axial direction of the operation wire 50 in the first bending portion 23a, and the operation wire 50 is held by the holding members 45. Thus, the operation wire 50 is guided by the wire guide member 101 in the second bending portion 23b, and is held by the holding members 45 in the first bending portion 23a.

As described above, the distal end portion of the operation wire 50 is connected to the distal rigid portion 21. The operation wire 50 is inserted through the first bending portion 23a, the second bending portion 23b, the flexible tube portion 25, and the main body portion 61. The proximal end portion of the operation wire 50 is connected to the bending operation mechanism.

[Regulation Wire 103]

As shown in FIG. 2, the regulation wire 103 is inserted through the bending portion 23 (the first bending portion 23a and the second bending portion 23b). The regulation wire 103 regulates the bending of the bending portion 23 so that the second bending portion 23b is bent in a direction opposite to the bending direction of the first bending portion 23a as shown in FIG. 6B and the bending portion 23 is bent in an S-shape when the first bending portion 23a is bent as shown in FIG. 6A. The regulation wire 103 is separate from the operation wire 50. As shown in FIG. 2, the regulation wire 103 is longer than the bending portion 23.

For example, one regulation wire 103 is provided. The regulation wire 103 is provided to face one operation wire 50 as shown in FIG. 2 and FIG. 3C in the diametrical direction of the bending portion 23 (joint ring 30) in order to regulate the bending of the bending portion 23 as described above. The regulation wire 103 has a tensile strength and a breaking strength equal to or more than those of the operation wire 50 in order to regulate the bending of the bending portion 23 as described above. Therefore, for example, the diameter of the regulation wire 103 is larger than the diameter of the operation wire 50, as shown in FIG. 3C. The regulation wire 103 is made of a material having bending elasticity so that the bending portion 23 can be bent when the bending portion 23 is bent.

As shown in FIG. 2, FIG. 6A, and FIG. 6B, the regulation wire 103 moves back and forth relative to the bending portion 23 along the axial direction of the regulation wire 103 when the bending portion 23 is bent and when the bending portion 23 is restored to a straight state from a bent state. In the present embodiment, as shown in FIG. 2, for example, a distal end portion 103a of the regulation wire 103 is fixed to the distal rigid portion 21. This fixing is, for example, welding, deposition, or caulking. The distal end portion 103a is formed as a fixed end. As shown in FIG. 2, when the bending portion 23 has a natural length and is stretched straight, a proximal end portion 103b of the regulation wire 103 is provided inside the mouthpiece 26 of the flexible tube portion 25 coupled to the joint ring 31b. The proximal end portion 103b is formed as a free end. As the distal end portion 103a of the regulation wire 103 is fixed as described above, the proximal end portion 103b of the regulation wire 103 moves relative to the bending portion 23 toward the distal rigid portion 21 along the axial direction of the regulation wire 103 when the bending portion 23 is bent. When the bending portion 23 is restored to the straight state from the bent state, the proximal end portion 103b of the regulation wire 103 moves relative to the bending portion 23 toward the mouthpiece 26 of the flexible tube portion 25 along the axial direction.

The regulation wire 103 is held by a holding member 45a so that the regulation wire 103 is movable (slidable) back and forth relative to the holding member 45a in the axial direction of the regulation wire 103 as shown in FIG. 2 and FIG. 3C when the bending portion 23 is bent and when the bending portion 23 is restored to the straight state from the bent state. The holding member 45a is substantially similar in configuration to the holding member 45, and is separate from the holding member 45. The holding member 45a is provided in each of the joint rings 30 in the first bending portion 23a and the second bending portion 23b, and the holding member 45a is fixed to the inner circumferential surface 30a of each of the joint rings 30, for example, by welding. As shown in FIG. 3C, the holding member 45a is provided out of alignment with the holding member 45 in the circumferential direction of the bending portion 23 (joint ring 30).

The mouthpiece 26 of the flexible tube portion 25 has, on its edge, a cutout portion 26a into which the holding member 45a is fitted as shown in FIG. 4 to prevent the edge of the mouthpiece 26 from contacting the holding member 45a when fitted into the joint ring 31b.

As shown in FIG. 2, the regulation wire 103 is not guided by the wire guide member 101.

As shown in FIG. 2 and FIG. 4, the regulation wire 103 has a prevention portion 105 provided in the proximal end portion 103b of the regulation wire 103. When the bending portion 23 is bent as shown in FIG. 6A so that the regulation wire 103 moves toward the distal rigid portion 21, the prevention portion 105 contacts the holding member 45a, and thereby regulates the bending of the bending portion 23 as shown in FIG. 6B and prevents the regulation wire 103 from coming off the joint ring 31b. This prevention portion 105 has, for example, a cylindrical member to cover the proximal end portion 103b. The prevention portion 105 is fitted in, for example, the proximal end portion 103b, and is thicker than the holding member 45a. When the bending portion 23 is bent as shown in FIG. 6A so that the proximal end portion 103b of the regulation wire 103 moves toward the distal rigid portion 21, the prevention portion 105 contacts the holding member 45a provided in the joint ring 31b. The prevention portion 105 thereby prevents the regulation wire 103 from coming off the joint ring 31b, and regulates the bending of the bending portion 23 as shown in FIG. 6B.

[Length L]

As shown in FIG. 2, when the bending portion 23 is straight, the proximal end portion 103b of the regulation wire 103 projects a desired length L from the joint ring 31b toward the mouthpiece 26 of the flexible tube portion 25. The desired length L is calculated as below.

As shown in FIG. 6B, for example, the radius of the joint ring 30 is r.

As shown in FIG. 6B, the bending radius of the first bending portion 23a is R1 when the bending portion 23 is bent in an S-shape.

As shown in FIG. 6B, the bending radius of the second bending portion 23b is R2 when the bending portion 23 is bent in an S-shape.

When the bending portion 23 is bent in an S-shape and the first bending portion 23a is further bent after the prevention portion 105 has contacted the holding member 45a, the bending angle of the first bending portion 23a is $\theta1$.

When the bending portion 23 is bent in an S-shape and the second bending portion 23b is bent after the prevention portion 105 has contacted the holding member 45a, the bending angle of the second bending portion 23b is $\theta2$.

In this case, the stretch amount $r\theta1$ of the first bending portion 23a = the contraction amount $r\theta2$ of the second bending portion 23b.

When R1=R2, $\theta1=\theta2$.

If the bending angle of the whole first bending portion 23a is $\theta0$, the bending angle of the first bending portion 23a is $\theta0-\theta1$ when the first bending portion 23a is bent until the prevention portion 105 contacts the holding member 45a.

The stretch amount of the first bending portion 23a in this case is $r(\theta0-\theta1)$.

The above-mentioned desired length L is $r(\theta0-\theta1)$.

[Difference L3]

When the first bending portion 23a and the second bending portion 23b are bent in the same direction as shown in FIG. 5A, a difference L3 between the contracted inner operation wire 50 and the stretched outer operation wire 50 is calculated as below.

A curvature R1 of the inner circumferential surface is R0−r. R1 indicates the curvature of the inner operation wire 50.

A curvature R2 of the outer circumferential surface is R0+r. R2 indicates the curvature of the outer operation wire 50.

R0 indicates the curvature of the bending portion 23, and P1/2/tan $\theta3$.

Figure 5B:
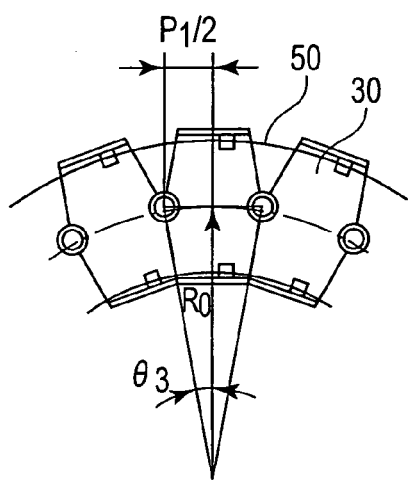
FIG. 5B is a schematic diagram for calculating the difference L3 between the contracted inner operation wire and the stretched outer operation wire when the bending portion is bent.

As shown in FIG. 5B, P1 indicates a length of an axial direction of the joint ring 30. $\theta3$ indicates the bending angle of the joint ring 30.

A length L0 of an arc of R0 is $R0\theta4$.

A length L1 of an arc of R1 is $R1\theta4$.

A length L2 of an arc of R2 is $R2\theta4$.

$\theta0$ indicates a bending angle.

In this case, the difference L3 between the contracted inner operation wire 50 and the stretched outer operation wire 50 is $L2-L1=(R2-R1)\theta4=2r\theta4$.

[Operation Method]

Now, an operation method according to the present embodiment is described.

Here, the regulation wire 103 is provided to face the downward operation wire 50, and provided adjacent to the upward operation wire 50.

For example, if the vertical bending operation knob 67b is operated, the downward operation wire 50, for example, is pulled, and the bending portion 23 is bent, for example, downward as shown in FIG. 6A. At the same time, the first bending portion 23a is bent downward before the second bending portion 23b as shown in FIG. 6A because the wire guide member 101 is provided in the second bending portion 23b. The second bending portion 23b still remains straight.

Moreover, at the same time, the downward operation wire 50 is disposed on the inner side of the bent bending portion 23, and the upward operation wire 50 (not shown) and the regulation wire 103 are disposed on the outer side of the bent bending portion 23. As a result, the proximal end portion 103b of the regulation wire 103 moves relative to the bending portion 23 toward the distal rigid portion 21 along the axial direction of the regulation wire 103.

More specifically, the path length of the outer circumferential side (the side of the regulation wire 103) of the bending portion 23 is greater than the path length of the inner circumferential side (the side of the downward operation wire 50) of the bending portion 23. Therefore, if the first bending portion 23a is bent as shown in FIG. 6A, the proximal end portion 103b of the regulation wire 103 is retracted toward the distal rigid portion 21. As the regulation wire 103 is made of a material having bending elasticity, the regulation wire 103 bends along the bending shape of the first bending portion 23a while being retracted.

The regulation wire 103 has a tensile strength and a breaking strength equal to or more than those of the operation wire 50. Therefore, for example, the diameter of the regulation wire 103 is larger than the diameter of the operation wire 50. Thus, the first bending portion 23a is not easily bent because of the regulation wire 103, and a constant path length on the outer circumferential side of the bending portion 23 is maintained. In this way, the bending of the bending portion 23 is regulated by the regulation wire 103.

The proximal end portion 103b of the regulation wire 103 is retracted toward the distal rigid portion 21 to ensure that the prevention portion 105 contacts the holding member 45a provided in the joint ring 31b. This ensures that a constant path length on the outer circumferential side of the bending portion 23 is maintained. In this way, the bending of the bending portion 23 is regulated by the regulation wire 103.

In this condition, if the vertical bending operation knob 67b is further operated and the downward operation wire 50, for example, is further pulled, the first bending portion 23a is further bent. However, the regulation wire 103 has a tensile strength and a breaking strength equal to or more than those of the operation wire 50, and the prevention portion 105 is in contact with the holding member 45a, so that a constant path length on the outer circumferential side of the bending portion 23 is maintained. Therefore, more force is applied to the outer circumferential side (the side of the regulation wire 103) of the bending portion 23 than the inner circumferential side (the side of the downward operation wire 50) of the bending portion 23. Thus, force is applied to the second bending portion 23b in a direction (upward direction) opposite to the first bending portion 23a, and the second bending portion 23b is bent to the side (upper side) opposite to the first bending portion 23a. As a result, the bending portion 23 is bent in an S-shape, as shown in FIG. 6B. In this case, the second bending portion 23b is first bent at its distal end (the side of the joint ring 31d) rather than at its proximal end (the side of the joint ring 31b).

Thus, when the first bending portion 23a is bent, the regulation wire 103 regulates the bending of the bending portion 23 to ensure that the second bending portion 23b is bent in a direction opposite to the bending direction of the first bending portion 23a and that the bending portion 23 is bent in an S-shape because the regulation wire 103 has a tensile strength and a breaking strength equal to or more than those of the operation wire 50 and the prevention portion 105 contacts the holding member 45a.

Then the distal rigid portion 21 is moved by the bending of the first bending portion 23a, and moved to be pulled back by the bending of the second bending portion 23b. Consequently, the position of the distal rigid portion 21 is changed, and, for example, the direction of the imaging unit is changed so that the observation target is caught in the imaging field of the imaging unit.

[Advantageous Effects]

As described above, in the present embodiment, the first bending portion 23a and the second bending portion 23b are formed in the bending portion 23 by the wire guide member 101. Moreover, in the present embodiment, the regulation wire 103 is provided to face one operation wire 50 in the diametrical direction of the bending portion 23 (joint ring 30), and has a tensile strength and a breaking strength equal to or more than those of the operation wire 50. Therefore, in the present embodiment, a constant path length on the outer circumferential side of the bending portion 23 can be maintained, the bending of the bending portion 23 is regulated by the regulation wire 103, and the second bending portion 23b can be bent in a direction opposite to the bending direction of the first bending portion 23a.

Consequently, in the present embodiment, the bending portion 23 can be readily bent in an S-shape by one bending operation portion 67.

In the present embodiment, the distal end portion 103a of the regulation wire 103 is fixed to the distal rigid portion 21, and the proximal end portion 103b of the regulation wire 103 is movable. In the present embodiment, the regulation wire 103 is longer than the bending portion 23, and the proximal end portion 103b of the regulation wire 103 has the prevention portion 105. In the present embodiment, the prevention portion 105 contacts the holding member 45a when the bending portion 23 is bent. In the present embodiment, this ensures that a constant path length on the outer circumferential side of the bending portion 23 can be maintained, the second bending portion 23b can be bent in a direction opposite to the bending direction of the first bending portion 23a, and the bending portion 23 can be readily bent in an S-shape by one bending operation portion 67.

In the present embodiment, the wire guide member 101 is provided in the second bending portion 23b to ensure that the first bending portion 23a can be bent before the second bending portion 23b.

In the present embodiment, the regulation wire 103 is made of a material having bending elasticity so that the bending portion 23 can be bent when the bending portion 23 is bent. In the present embodiment, this ensures that the bending portion 23 can be bent.

[First Modification]

Figure 7A:
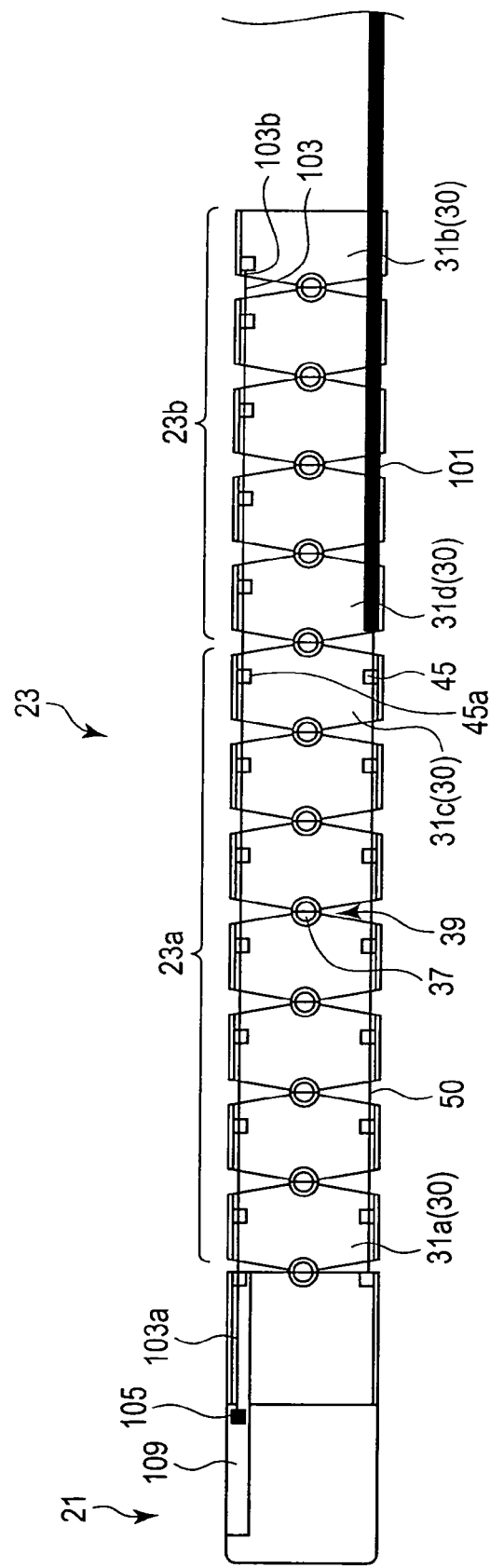
FIG. 7A is a diagram simply showing the structure of the bending portion according to a first modification.
Figure 7C:
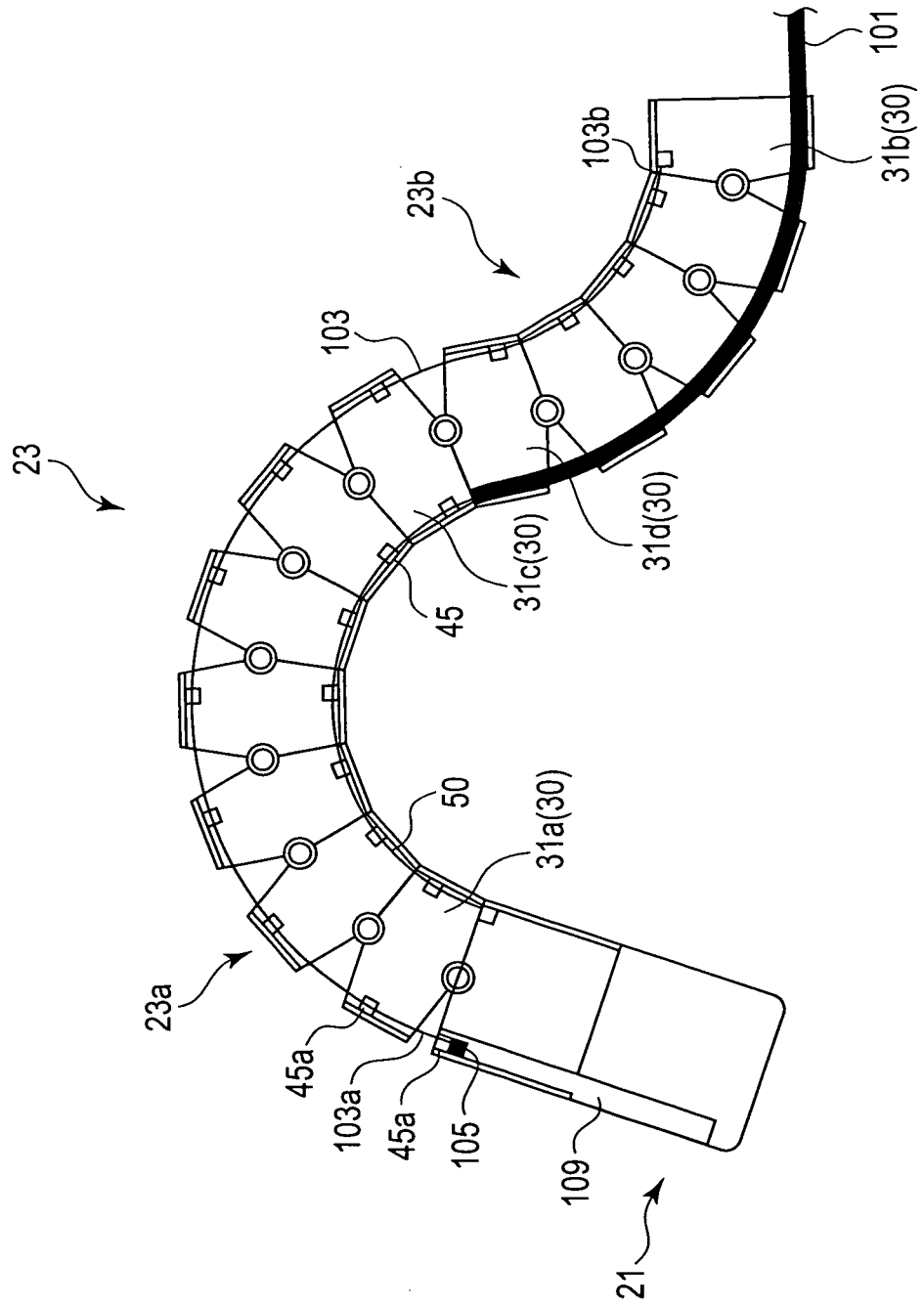
FIG. 7C is a schematic diagram in which the bending portion is bent in an S-shape.

Now, a first modification of the embodiment is described with reference to FIG. 7A, FIG. 7B, and FIG. 7C.

In the embodiment, the distal end portion 103a of the regulation wire 103 is fixed to the distal rigid portion 21, the proximal end portion 103b of the regulation wire 103 is movable, and the proximal end portion 103b of the regulation wire 103 has the prevention portion 105. However, the present invention does not need to be limited to this as long as the bending portion 23 can be bent in an S-shape by one bending operation portion 67.

For example, the proximal end portion 103b of the regulation wire 103 is fixed to the joint ring 31b. The distal end portion 103a of the regulation wire 103 is formed as a free end, and is movable along the axial direction of the regulation wire 103. The distal end portion 103a of the regulation wire 103 has the prevention portion 105. As shown in FIG. 7B, the prevention portion 105 contacts the holding member 45a provided in the distal rigid portion 21 when the bending portion 23 is bent.

In this case, the distal rigid portion 21 has a groove portion 109 in which the prevention portion 105 can slide along the axial direction of the regulation wire 103. The length of this groove portion 109 is the above-mentioned r(θ0−θ1).

Alternatively, for example, the distal end portion 103a and the proximal end portion 103b of the regulation wire 103 may be formed as free ends, and movable along the axial direction of the regulation wire 103. In this case, the distal end portion 103a and the proximal end portion 103b of the regulation wire 103 may have the prevention portions 105.

Thus, in the present modification, at least one of the distal end portion 103a and the proximal end portion 103b of the regulation wire 103 has only to be formed as a free end so that the regulation wire 103 is movable along the axial direction of the regulation wire 103, and the free end has only to have the prevention portion 105.

[Second Modification]

Now, a second modification of the embodiment is described with reference to FIG. 8.

In the embodiment, the diameter of the regulation wire 103 is larger than the diameter of the operation wire 50. However, the present invention does not need to be limited to this as long as the regulation wire 103 has a tensile strength and a breaking strength equal to or more than those of the operation wire 50.

As shown in FIG. 8, for example, when the operation wire 50 and the regulation wire 103 are formed by bundles of wires, the number of the wires bundled in the regulation wire 103 has only to be larger than the number of the wires bundled in the operation wire 50.

Alternatively, for example, the regulation wire 103 has only to have a larger amount of a high tensile- and breaking-strength material such as tungsten than the operation wire 50.

Alternatively, the stretchability of the regulation wire 103 has only to be lower than the stretchability of the operation wire 50. Alternatively, the elasticity of the regulation wire 103 has only to be lower than the elasticity of the operation wire 50.

[Third Modification]

Now, a third modification of the embodiment is described with reference to FIG. 9.

In the embodiment, the operation wire 50 is separate from the regulation wire 103, but may double as the regulation wire 103 as in the present modification. In this case, the operation wire 50 has, for example, the prevention portion 105 located a predetermined length apart from the holding member 45a of the joint ring 31b toward the mouthpiece 26 of the flexible tube portion 25 when the bending portion 23 is straight. The wire guide member 101 is provided up to the side of the holding member 45a of the joint ring 31b, and is not provided in the bending portion 23. The inside diameter of the wire guide member 101 is substantially the same as the inside diameter d2 of the prevention portion 105. Therefore, a wire guide member 101a having the same inside diameter d1 as the outside diameter d1 of the wire guide member 101 is provided at the distal end portion of the wire guide member 101. The wire guide member 101a is fixed to the distal end portion of the wire guide member 101, for example, by welding. The wire guide member 101a is provided up to the holding member 45a of the joint ring 31b from the distal end portion of the wire guide member 101, and is not provided in the bending portion 23. The inside diameter d1 of the wire guide member 101a is larger than the outside diameter d2 of the prevention portion 105 and the inside diameter d3 of the holding member 45a.

Thus, the operation wire 50 doubles as the regulation wire 103 while being guided up to the bending portion 23 by the wire guide members 101 and 101a. The prevention portion 105 can axially slide the wire guide member 101a together with the regulation wire 103 (operation wire 50).

Thus, in the present modification, the operation wire 50 doubles as the regulation wire 103, so that the number of components can be reduced, and the bending portion 23 can be reduced in diameter.

[Fourth Modification]

Now, a fourth modification of the embodiment is described with reference to FIG. 10A.

In the embodiment, the holding member 45 which holds the operation wire 50 and the holding member 45a which holds the regulation wire 103 are separate in the first bending portion 23a. However, the present invention does not need to be limited to this.

For example, as in the present modification, the holding member 45 may integrally hold the operation wire 50 and the regulation wire 103. Thus, in the present modification, the holding member 45a can be omitted, and the number of processes in the fabrication of the bending portion 23 can be reduced.

[Fifth Modification]

Now, a fifth modification of the embodiment is described with reference to FIG. 10B.

In the embodiment, the holding member 45 which holds the operation wire 50 is provided out of alignment in the circumferential direction with the holding member 45a which holds the regulation wire 103 in the first bending portion 23a. However, the present invention does not need to be limited to this.

For example, as in the present modification, the holding member 45 and the holding member 45a may overlap so that the operation wire 50 and the regulation wire 103 do not overlap in the axial direction of the bending portion 23. Thus, in the present modification, the bending portion 23 can be reduced in diameter.

The present invention is not completely limited to the embodiment described above, and modifications of components can be made at the stage of carrying out the invention without departing from the spirit thereof. Various inventions can be made by a proper combination of the components disclosed in the embodiment described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   a distal rigid portion comprising an imaging unit configured to image an observation target;
   a bending portion comprising a first bending portion coupled to the distal rigid portion and a second bending portion coupled to the proximal end portion of the first bending portion;
   a flexible tube portion coupled to the proximal end portion of the second bending portion;
   an operation wire which is connected to the distal rigid portion and which is inserted through the first bending portion, the second bending portion, and the flexible tube portion;
   a wire guide member comprising a distal end fixed to the inside of the distal end of the second bending portion, the wire guide member being inserted through the second bending portion and the flexible tube portion the wire guide member guiding the operation wire when the operation wire is inserted through the wire guide member;
   a bending operation portion which is connected to the operation wire and which bends and operates the first bending portion when the bending operation portion pulls the operation wire; and
   a regulation wire, the regulation wire being longer than the bending portion, the regulation wire being inserted through the first bending portion and the second bending portion, the regulation wire being provided to face the operation wire in the diametrical direction of the bending portion, the regulation wire regulating the bending of the bending portion so that the second bending portion is bent in a direction opposite to the bending direction of the first bending portion and the bending portion is bent in an S-shape when the first bending portion is bent, wherein
   the first bending portion and the second bending portion comprise holding members which hold the regulation wire,
   at least one of the distal end portion and the proximal end portion of the regulation wire is formed as a free end so that the regulation wire is movable along the axial direction of the regulation wire, and
   the free end comprises a prevention portion which contacts the holding member, and thereby regulates the bending of the bending portion and prevents the regulation wire from coming off the bending portion.

2. The endoscope according to claim 1, wherein the diameter of the regulation wire is larger than the diameter of the operation wire.

3. The endoscope according to claim 2, wherein when the operation wire and the regulation wire are formed by bundles of wires, the number of the wires bundled in the regulation wire is larger than the number of the wires bundled in the operation wire.

4. The endoscope according to claim 3, wherein the regulation wire has a tensile strength and a breaking strength equal to or more than those of the operation wire.

5. The endoscope according to claim 4, wherein the stretchability of the regulation wire is lower than the stretchability of the operation wire.

6. The endoscope according to claim 5, wherein the elasticity of the regulation wire is lower than the elasticity of the operation wire.

7. The endoscope according to claim 6, wherein more than one operation wire is provided to face each other in the diametrical direction of the bending portion, and one of the operation wires doubles as the regulation wire.

* * * * *